US009788754B2

(12) United States Patent
Vilsmeier

(10) Patent No.: US 9,788,754 B2
(45) Date of Patent: Oct. 17, 2017

(54) METHOD OF MANAGING A BRAIN STROKE

(71) Applicant: Brainlab AG, Feldkirchen (DE)

(72) Inventor: Stefan Vilsmeier, Munich (DE)

(73) Assignee: Brainlab AG, Munich (DE)

( * ) Notice: Subject to any disclaimer, the term of this patent is extended or adjusted under 35 U.S.C. 154(b) by 22 days.

(21) Appl. No.: 14/279,357

(22) Filed: May 16, 2014

(65) Prior Publication Data

US 2015/0327817 A1 Nov. 19, 2015

(51) Int. Cl.
*A61B 5/05* (2006.01)
*A61B 5/055* (2006.01)
*A61B 6/04* (2006.01)
*A61B 6/00* (2006.01)
*A61B 5/00* (2006.01)
*A61B 6/03* (2006.01)

(52) U.S. Cl.
CPC ............ *A61B 5/055* (2013.01); *A61B 5/0073* (2013.01); *A61B 5/0082* (2013.01); *A61B 6/032* (2013.01); *A61B 6/0407* (2013.01); *A61B 6/501* (2013.01); *A61B 6/504* (2013.01); *A61B 5/0555* (2013.01)

(58) Field of Classification Search
CPC . A61B 18/1492; A61B 18/24; A61B 19/5244; A61K 38/55; A61K 2300/00
See application file for complete search history.

(56) References Cited

U.S. PATENT DOCUMENTS

| 5,304,383 | A | * | 4/1994 | Eibl | A61K 38/55 424/499 |
| 5,822,814 | A | * | 10/1998 | Van der Ende | A61B 6/04 378/179 |
| 9,155,912 | B2 | * | 10/2015 | Yu | A61N 5/10 |
| 2012/0101371 | A1 | * | 4/2012 | Verdooner | A61B 3/12 600/425 |
| 2012/0198624 | A1 | * | 8/2012 | Zheng | A61B 6/0457 5/601 |
| 2012/0215094 | A1 | * | 8/2012 | Rahimian | A61B 1/00193 600/414 |

(Continued)

*Primary Examiner* — Baisakhi Roy
(74) *Attorney, Agent, or Firm* — Tucker Ellis LLP

(57) ABSTRACT

The present invention relates to a medical method of managing a cerebrovascular insult, the method comprising the following steps in this order:
a) placing a patient on a patient support unit;
b) positioning a mobile tomographic imaging system in a predetermined position relative to the patient support unit with the patient placed on the patient support unit;
c) imaging at least part of the patient's brain using an imaging unit of the tomographic imaging system, the imaging comprising in particular generating an image describing the functioning of the patient's blood vessel system;
d) determining, in dependence on the result of the imaging,
whether the patient support unit should be rotated relative to the tomographic imaging system with the patient placed on the patient support unit so that the patient is free of the imaging unit in order to conduct a medical intervention on the patient's blood vessel system, or
whether the patient support unit may remain in its position relative to the tomographic imaging system with the patient placed on the patient support unit.

19 Claims, 3 Drawing Sheets

(56) References Cited

U.S. PATENT DOCUMENTS

2013/0235969 A1\* 9/2013 Winter ............... G01R 33/4808
378/4
2014/0155740 A1\* 6/2014 Semenov ............. A61B 5/0073
600/425

\* cited by examiner

METHOD OF MANAGING A BRAIN STROKE

BACKGROUND

The present invention relates to the field of managing a brain stroke (also called cerebrovascular insult or brain attack). In particular, the present invention is directed to a medical method for deciding how to manage the therapy of a stroke.

A stroke is a disease in which a patient's brain is not sufficiently supplied with blood at least at certain locations in the brain. The affected brain regions may therefore suffer from hypoxemia which will lead to cell death in the respective brain regions and loss of their corresponding neurologic function.

In general, two different kinds of stroke have to be considered. The first kind of stroke is called ischemic stroke and is caused a blockage of a blood vessel supplying blood, oxygen and nutrients to the brain. The blockage thus in general is an arterial embolism in an artery leading to the brain. The other kind of stroke is called hemorrhagic stroke and is defined as a hemorrhage from a blood vessel into the brain. A hemorrhagic stroke may be caused by a ruptured aneurysm in the brain or other medical indications involving the rupture of a blood vessel in the brain (for example arteriovenous malformation or in the case of blunt or open head trauma where exertion of an external force exerted onto the brain may lead to such a rupture). Due to a continuing flow of blood into the brain and a closed volume available for accommodating the brain (the volume being defined by the patient's skull), a hemorrhage into brain tissue will cause the brain pressure (intracranial pressure—ICP) to rise. An increase of intracranial pressure, however, in general leads to destruction of brain cells and corresponding loss of brain function.

Since different approaches are applied for therapy of these two kinds of stroke, and since a potentially time-dependent loss of brain function should be avoided, it is of great importance to quickly diagnose which kind of stroke a patient is suffering from. A quick diagnosis will allow reducing the time until a vessel blockage is removed in order to allow the respective brain region to be supplied with blood again, or until the patient can undergo craniotomy in order to reduce the intracranial pressure.

A present approach to diagnosis includes generating a magnetic resonance angiography or computed tomography angiography of the patient's brain. From the resulting image, a physician can then judge what kind of stroke the patient is suffering from.

Once the kind of stroke has been diagnosed, the patient can undergo further therapy. Presently, the patient has to be placed onto a bed which is fixedly attached to a magnetic resonance tomograph or computer x-ray tomograph for generating the angiography. However, in order to conduct the therapy, the patient will have to be removed from the tomograph and be taken to an operating room or other units of a health care institution. The resulting time required for removing the patient from the tomograph, placing him on a mobile bed and transporting him to the operating room or other unit necessarily delays therapy.

Therefore it is an object of the present invention to provide a method of managing a stroke which avoids or at least reduces a time delay between diagnosis and therapy.

The present invention is designed for use with angiography planning software supplied by Brainlab®.

SUMMARY OF THE INVENTION

In the following, a description of preferred features of the present invention is given which is not intended to limit the invention only to those features described in the following but rather serve explanatory purposes in order to support the reader's understanding of the general aspects of the invention.

In one embodiment, the invention includes a medical method of managing a cerebrovascular insult, the method comprising the following steps preferably in this order:
a) placing a patient on a patient support unit;
b) positioning a mobile tomographic imaging system in a predetermined position relative to the patient support unit with the patient placed on the patient support unit;
c) imaging at least part of the patient's brain using an imaging unit of the tomographic imaging system, the imaging comprising in particular generating an image describing the function of the patient's blood vessel system;
d) determining, in dependence on the result of the imaging,
   whether the patient support unit should be rotated relative to the tomographic imaging system with the patient placed on the patient support unit so that the patient is free of the imaging unit in order to conduct a medical intervention on the patient's blood vessel system or
   whether the patient support unit may remain in its position relative to the tomographic imaging system with the patient placed on the patient support unit.

Within the framework of this application, the term of imaging encompasses generating of an image using the image modality which the tomographic imaging system is configured to apply. If the tomographic imaging apparatus is a magnetic resonance tomograph, the imaging therefore encompasses generating a magnetic resonance tomography image, if the imaging system is an x-ray-based computed tomography scanner, the imaging therefore encompasses generating a computed tomography image. Specifically, it is determined, as a result of the imaging, whether the patient suffers from an ischemic stroke or a hemorrhagic stroke. The step of imaging may according to an embodiment encompass also more sequence of imaging steps. For example, a first imaging may be conducted which is followed by a second imaging. The first imaging may serve to determine the general pathologic state of the patient (i.e. what kind of stroke the patient is suffering from), the second imaging may support execution of the medical intervention (e.g. checking the success of the medical intervention). The first imaging may be a computed x-ray tomography, the second imaging may then be a computed x-ray tomography angiography (CTA). Alternatively, the first imaging may be a magnetic resonance tomography, the second imaging may then be a magnetic resonance tomography angiography (MRA).

Specifically, positioning the tomographic imaging system (in particular, an imaging unit of the tomographic imaging system such as a gantry comprising emitters and detectors imaging radiation) in a predetermined position relative to the patient support unit comprises fastening the patient support unit with the patient placed on the patient support unit to a pedestal of the tomographic imaging system. The pedestal preferably has a known (in particular predetermined) position relative to the tomographic imaging system, in particular relative to the imaging unit of the tomographic imaging system, and preferably is rotatable around a vertical axis and rotatable relative to the imaging unit. Further preferably, the pedestal is an integral part of the mobile tomographic system. The aforementioned feature that the pedestal preferably is rotatable around a vertical axis (preferably by at least substantially) 90° and rotatable relative to the imaging unit means that at least part of the pedestal is rotatable in the aforementioned ways. Alternatively to the pedestal being rotatable, the patient support unit, such as a bed (in particular, flat bad) may be rotatable once it has been fastened to the pedestal and is supported by the pedestal around a vertical axis and relative to the imaging unit. Further specifically, the predetermined position of the pedestal relative to the imaging unit is a fixed position. However, the imaging unit may be constituted to be translatable and rotatable relative to a movable base unit of the mobile tomographic imaging system, and the pedestal is preferably attached to the base unit at a fixed position. The base unit can also be motorized to ease transport of the mobile tomographic imaging system.

Specifically, the patient support unit can be detachably fastened to the aforementioned pedestal. However, it will not be necessary to detach the patient support unit from the pedestal for rotation of the patient support unit with the patient placed on it. The patient will remain placed on the patient support unit after the rotation at least until the medical intervention has been completed.

According to specific embodiments, the imaging unit comprises a scanner configured to generate a tomography. The tomography may be a magnetic resonance tomography, in particular a magnetic resonance-based angiography (such as a magnetic resonance angiography—MRA). Alternatively, the tomography may be a computed x-ray tomography, in particular a computed x-ray tomography based angiography (such as a computed tomography angiography—CTA). Specifically, the imaging includes generating an angiography of at least part of the patient's brain, in particular one of the aforementioned types of angiography.

Specifically, the patient support unit is a bed or a flat table. Preferably, the patient support unit is mobile in the sense that it can be attached to a moving unit such as a set of wheels. Preferably, the patient support unit is detachably attached to such a moving unit and can be placed onto the aforementioned pedestal, fastened to the pedestal and then separated from the moving unit, the moving unit then being drawn away from the mobile tomographic imaging system. Further specifically, the patient support unit is translucent for x-rays so as to allow generation of an x-ray-based computed tomography of the patient with a patient being placed on the patient support unit. The phrase "with a patient placed on the patient support unit" in the framework of the present application encompasses that the patient is placed on the patient support unit and remains in that state while another action is being conducted.

According to one further specific embodiment, placing the tomographic imaging system in a predetermined position relative to the patient support unit comprises leaving the patient support unit stationary, in particular in a global reference system, and moving the tomographic imaging system towards the patient support unit, in particular in the global reference system. The aforementioned global reference system in this context serves to define the positions of both the patient support unit and the imaging unit and preferably does not have its origin in the patient support unit. The position in which the imaging unit is placed relative to the patient support unit is generally predetermined only to the extent that this position should allow generating an image of at least part of the patient's brain. For example, the mobile tomographic imaging system may be moved towards a bed in which a patient is lying so that it reaches a position in which it may be used to image the patient's brain (in the following also called "imaging position"). This does not necessarily encompass fastening the patient support unit to a pedestal or any other part of the mobile tomographic imaging system. In particular the mobile tomographic imaging system may not have such a pedestal at all. Preferably, the mobile tomographic imaging system is brought into a room in which the patient is lying on the patient support unit, and then the aforementioned steps of placing the imaging unit in a predetermined position relative to the patient support unit.

According to one embodiment, it is determined that the patient support unit should be rotated relative to the tomographic imaging system (in particular relative to the imaging unit) with the patient placed on the patient support unit. The medical intervention on the patient blood vessel system then preferably includes at least one of the following kinds of procedures:

systemic lysis therapy, local lysis therapy, angioplasty, stenting, vascular surgery, and inserting a catheter into the patient's blood vessel system. Insertion of a catheter may in particular include intracerebral catheter placement, for example for removing a blockage from inside the blood vessel system (such as a thrombus in a vein or an embolus in an artery). An example of such a procedure would be mechanical blood clot retrieval which includes inserting a forceps-like tool through the catheter into the blood vessel in order to get hold of the blood clot and remove it by retracting the tool through the catheter while the blood clot is grasped by the forceps. The aforementioned types of medical intervention are preferably conducted in the case of ischemic stroke.

at least one of vascular surgery and inserting a catheter into the patient's blood vessel system such as in intracerebral catheter placement in particular for stopping a hemorrhage. Stopping the hemorrhage may be achieved in particular by aneurysm coiling which can be assisted by placing a balloon or a stent, or aneurysm gluing or aneurysm clipping. Alternatively or additionally, the medical intervention may include direct puncturing of or open surgery on the patient's hemorrhagic area including in particular performing a craniotomy. One aim of direct puncturing and open surgery is to reduce brain pressure caused by the hemorrhage. The direct puncturing or open surgery may include using a catheter which is inserted into the patient's brain. In general, such a catheter must not come in contact with the blood vessel system. These types of medical interventions are preferably conducted in the case of hemorrhagic stroke.

In the following, a short explanation of the aforementioned kinds of medical intervention is given. Systemic lysis therapy includes giving the patient a pharmaceutical for thrombolysis in order to break down a blood clot blocking a blood vessel. This is generally achieved by giving the patient an intravenous infusion of analogs of tissue plasminogen activator (tPA) which is a protein that normally activates plasmin. Local lysis therapy works in a similar manner, with the difference that the pharmaceutical for breaking down the blood clot is not distributed throughout the whole of the patient's blood system. Rather, the pharmaceutical is applied only at the place where it is needed, namely at or adjacent to the position of the blood clot.

Angioplasty is a technique of mechanically widening narrowed or abstracted blood vessels, in particular arteries. The narrowing or abstraction, respectively, typically is a result of atherosclerosis. During angioplasty, generally an empty and collapsed balloon on a guide wire (known as a balloon catheter) is passed into the narrowed locations and then inflated to a preferably predetermined size in order to widen the blood vessel. Due to the expansion of the blood vessel, a blood clot/plaque deposit accumulated on the vessel wall may be removed or pushed away, thereby opening up the blood vessel for improved flow. The balloon is then normally deflated and withdrawn. A stent (i.e. a mechanical structure which typically has a cylindrical net-like shape and is designed to support the vessel wall) may or may not be inserted at the time of expanding the balloon to ensure that the vessel remains open after the balloon has been retracted.

Vascular surgery may encompass surgical closure of a ruptured blood vessel. Aneurysm coiling includes inserting a guiding catheter into the patient's arterial system up to a location close to an aneurysm (which may be located for example in the patient). Then, detachable coils made of for example platinum are inserted into the aneurysm using the inserted catheter. This leads to closure of the aneurysm. Instead of inserting coils into the aneurysm, the aneurysm may be filled with a glue which hardens and prevents the aneurysm from being filled with blood. Aneurysm clipping includes clipping the base of an aneurysm with a specially designed clip in order to decouple it from the blood flow. Currently, brain aneurysm clipping is typically carried out by craniotomy, however a new endoscopic endonasal approach is being tested. The medical invention may or may not be conducted within the framework of the present invention.

Specifically, the method in accordance with the invention may, if it is determined that the patient support unit should be rotated relative to the tomographic imaging system (in particular relative to the imaging unit) with the patient placed on the patient support unit, include rotating the patient support unit relative to the tomographic imaging system (in particular relative to the imaging unit, and preferably around a vertical axis—i.e. in a horizontal plane—and preferably by at least substantially 90°) with the patient placed on the patient support unit so that the patient is free of the imaging unit. In this position, the medical intervention can be conducted, and the position is therefore also called intervention position. The rotation may be performed while the patient support unit is fastened to the pedestal or with a patient support unit which is not fastened to the tomographic imaging system.

According to a further specific embodiment, the patient support unit may be rotated around the vertical axis into a position relative to the tomographic imaging system (in particular relative to the imaging unit) which allows to conduct an imaging of at least part of the patient's brain (i.e. into an imaging position) after the medical intervention has been conducted. The rotation of the patient support unit is preferably executed with a patient placed on the patient support unit. This further step of imaging may serve to verify, after the medical intervention has been completed, whether the medical intervention has been successful.

According to a further specific embodiment of the present invention, the method includes determining that the patient support unit may remain in its position relative to the tomographic imaging system (in particular relative to the imaging unit) with the patient placed on the patient support unit. If this is determined, a medical intervention may be conducted on the patient's blood vessel system with the patient support unit remaining in its position relative to the imaging unit with the patient placed on the patient support unit. Such a medical intervention then preferably is a kind of medical intervention which does not require space around the patient for executing that medical intervention. Such a medical intervention therefore allows the patient to remain inside the imaging unit (e.g. the gantry) of the mobile tomographic imaging system while the medical intervention is being conducted. An example of such a kind of medical intervention is a systemic lysis therapy. Therefore, the medical personal may decide whether it is necessary to move the patient away from the imaging unit or not once it has been determined that the patient should undergo systemic lysis therapy. In particular, it is up to the choice of the medical personal whether the patient should be moved relative to the imaging unit in this case or not.

The present invention provides for the advantage of using a mobile tomographic imaging system in stroke management such that it is not necessary to move the patient to a different room of a healthcare institution such as a hospital if it is determined that a certain type of medical intervention (in particular requiring a lot of space around the patient for its execution) has to be conducted for treatment of the stroke. This saves the time required for transport of the patient associated with the above-mentioned prior art approach. Furthermore, the patient need not be transported back into a room in which the tomographic imaging system is located after execution of the medical intervention in order to conduct further imaging for verification of therapeutic success.

BRIEF DESCRIPTION OF THE DRAWINGS

Other features and advantages of the present invention will be apparent from the following detailed description of the invention, taken into conjunction with the accompanying drawings, wherein.

DETAILED DESCRIPTION OF THE DRAWINGS

Figure 1C:
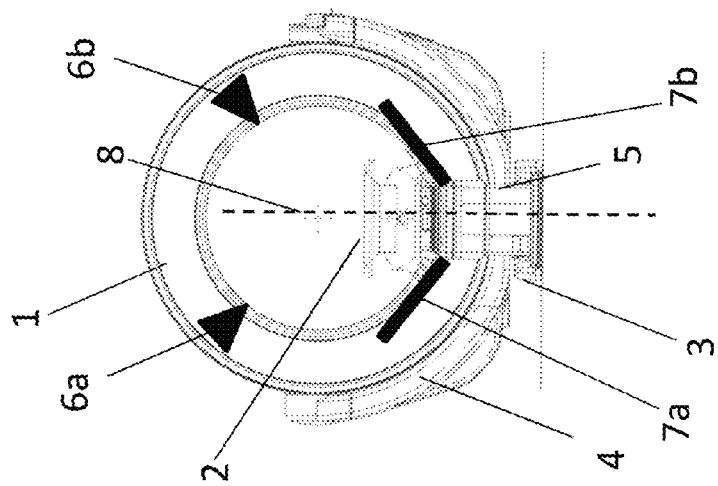
FIGS. 1a to 1c show three perspectives of a tomographic imaging system with the patient support unit placed on a pedestal of the tomographic imaging system.

The various embodiments will be described in detail with reference to the accompanying drawings. Wherever possible, the same reference numerals will be used throughout the drawings to refer to the same or like parts. References made to particular examples and implementations are for illustrative purposes, and they are not intended to limit the scope of the invention or the claims.

Figure 1B:
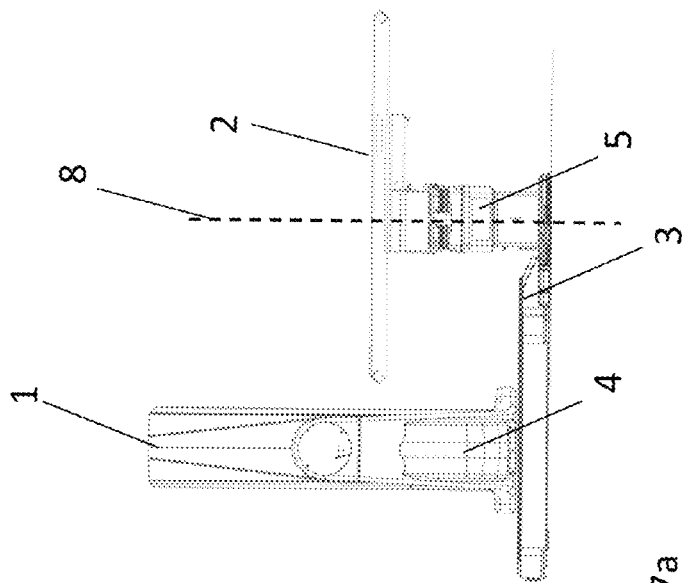
Figure 1A:
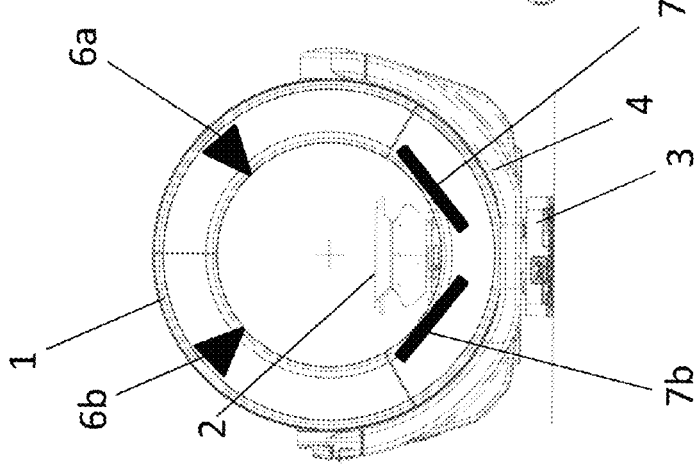

FIG. 1a is a view onto a tomographic imaging system from its rear, i.e. from the side opposite to the side on which a patient support unit embodied by a flat top table 2 is disposed during imaging. The tomographic imaging system in the case shown in the drawings is a computer tomograph operating on the basis of x-ray absorption and detection. The computer tomograph comprises an imaging unit comprised of a rigid circular rotor 1 having two x-ray radiation sources 6a and 6b and detector arrays 7a, 7b, the radiation sources 6a, 6b being disposed in the rotor 1 such that the x-rays emitted from the radiation sources 6a, 6b intersect each other at at least substantially a right angle. Opposite each of the radiation sources 6a, 6b (which may be embodied by x-ray tubes), each one detector array 7a, 7b is disposed in the rotor 1. The detector arrays 7a, 7b may be embodied by flat panel x-ray detectors. The system comprising the rotor 1, the x-ray sources 6a, 6b and detector arrays 7a, 7b (i.e. the imaging unit) is also called a gantry and is supported on a gimbal 4 such that the gantry can rotate around a horizontal axis which runs parallel to the plane of the flat top table 2. The gimbal 4 is movable disposed on a motorized base unit 3 which can be embodied by a set of motorized traction chains disposed in a housing. The gimbal 4 is disposed on the housing of the moving unit such that it can rotate around the vertical axis. Therefore, the gantry is able to move in two rotational degrees of freedom.

FIG. 1b illustrates a side view of this setup shown in FIG. 1a. As shown in FIG. 1b, a pedestal 5 is attached to the housing the base unit 3 at a fixed position relative to the housing. The flat top table 2 serving as a patient support unit can be mounted on the pedestal 5. Preferably, part of the pedestal 5 is rotatable around the vertical axis 8 running through the pedestal 5. This encompasses also the case in which not a part of the pedestal 5 is rotatable around the axis 8, but a mounting part of the flat top table 2 designed for attaching the flat top table 2 to the pedestal 5 allows for rotation of the flat top table 2 relative to the pedestal and/or the housing of the moving unit 3.

FIG. 1c is a frontal view of the setup shown in FIGS. 1a and 1b, i.e. from a side on which the flat top table 2 is supported on the pedestal 5 during an imaging operation, i.e. in the imaging position.

Figure 2:
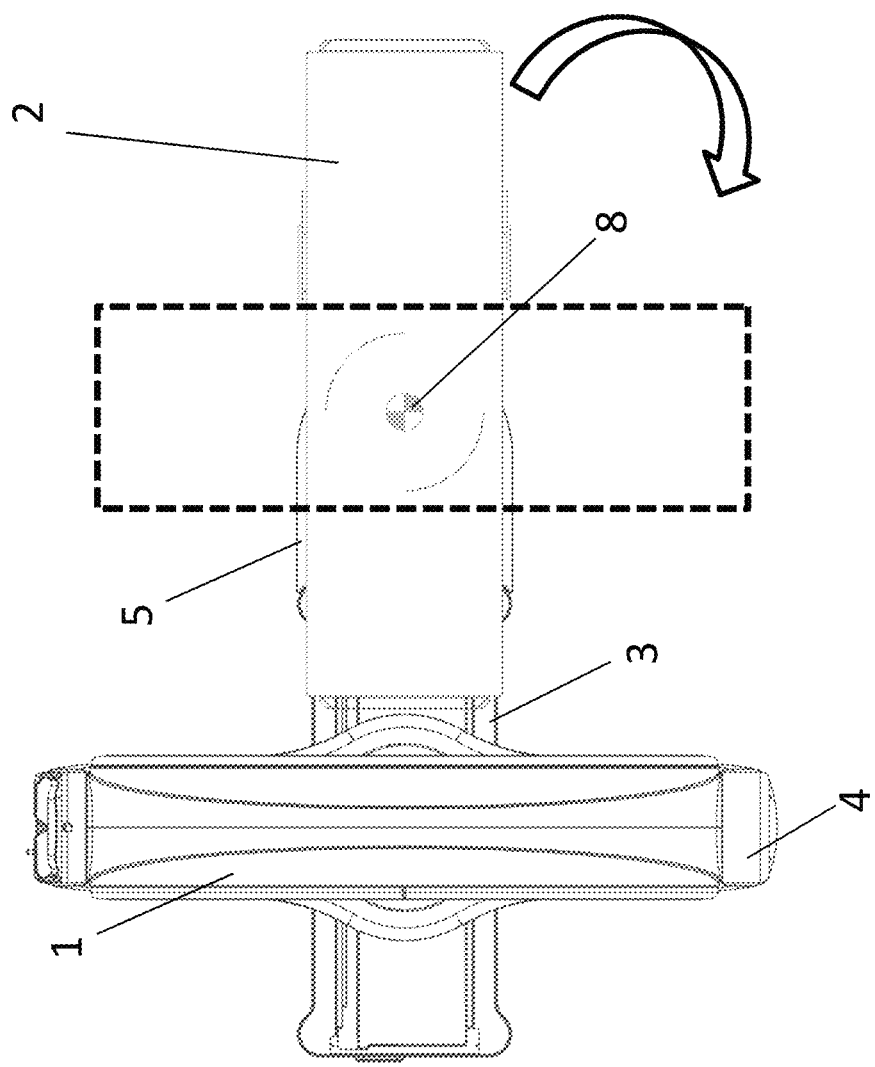
FIG. 2 illustrates rotation of the patient support unit around a vertical axis of the pedestal.

The flat top table 2 may be rolled on a wheel carriage (not shown) attached to the flat top table 2 onto the pedestal 5, fastened to the pedestal 5, and the wheel carriage may then be removed from the flat top table 2. Such a procedure constitutes one embodiment of positioning an imaging unit embodied by the aforementioned gantry in a predetermined position relative to a patient support unit embodied by the flat top table 2. Ideally, the patient is lying on the flat top table 2 when the flat top table 2 is placed on the pedestal 5. Then, at least part of the patient's brain is imaged using the imaging unit, and in dependence on the result of the imaging, it is decided whether the flat top table 2 should be rotated around the vertical axis 8. FIG. 2 illustrates a rotation (indicated by the arrow) of the flat top table 2 around the vertical axis 8 by 90° into the position of the flat top table indicated by the dashed black lines. The position indicated by the dashed lines is also called an intervention position, whereas the position of a flat top table shown in FIG. 1b is the imaging position. The intervention position is designed to allow maximum access to the patient for conducting a medical intervention serving therapy of the diagnosed pathologic state of the patient.

Figure 3:
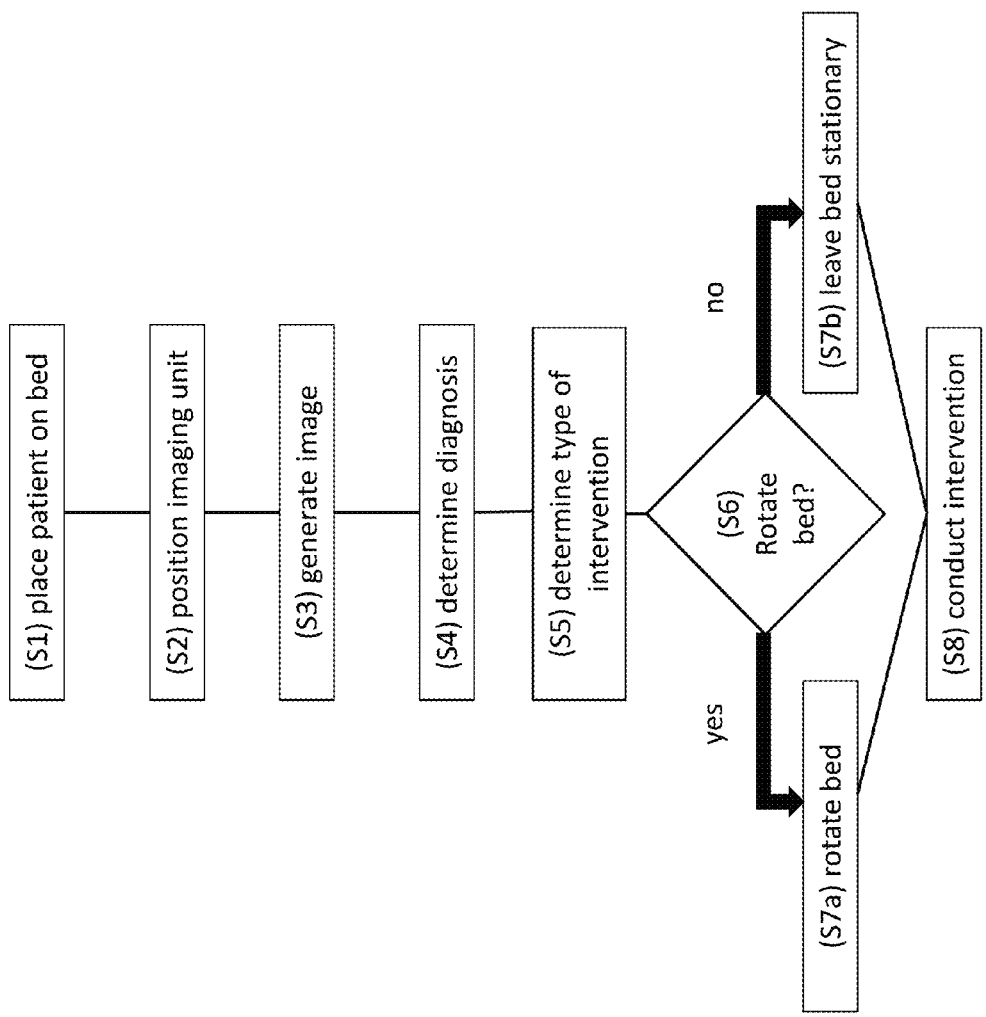
FIG. 3 is a flow diagram illustrating the sequence of steps of the method in accordance with the invention.

FIG. 3 is a flow chart explaining the flow of method steps in accordance with the invention.

In step S1, the patient is placed on a patient support unit embodied by the flat top table 2, and the imaging unit (for example the aforementioned gantry) is positioned in a predetermined position relative to the flat top table 2. It is once more noted that in order to do so, the flat top table 2 need not be positioned on a pedestal 5 of the tomographic imaging system. Rather, the tomographic imaging system may not have a pedestal 5, and the flat top table 2 may be supported on for example a wheel carriage. A mobile tomographic imaging system having a moving unit 3 and the aforementioned gantry may then be moved towards the flat top table 2 within the framework of step S2.

Once the flat top table 2 is in an imaging position relative to the imaging unit (i.e. relative to the gantry), an image of the patient's head is generated in step S3. This image serves as a basis for executing step S4 which is directed to determining a diagnosis for the patient. For example, the diagnosis can result in the patient having an ischemic stroke or a hemorrhagic stroke. In dependence on whether the patient has an ischemic stroke or a hemorrhagic stroke, the type of medical intervention required for therapy of the respective kind of stroke is determined in step S5. In dependence on the determined type of intervention (and therefore also in dependence on the diagnosis reached in step S4), it is determined in step S6 whether the patient support unit (i.e. the flat top table 2) should be rotated in order to conduct the determined type of intervention. If the answer to step S6 is yes, the bed is rotated in step S7a as shown in FIG. 2 into an intervention position. If the answer S6 is no, the flat top table 2 is left stationary in step S7b, i.e. the flat top table 2 is left in the imaging position.

After execution of steps S7a or S7b, respectively, the determined type of medical intervention is conducted in step S8. It is notable that not for all possible types of medical intervention, the answer to step S6 has to be yes. If the answer is no, it is determined that the patient support unit may remain in its position relative to the tomographic imaging system, in particular relative to the imaging unit (the gantry). Therefore, certain types of medical intervention such as a systemic lysis therapy may be conducted in the imaging position without hampering the medical intervention.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above-described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though no structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A medical method of managing a cerebrovascular insult, the method comprising:
   a) placing a patient on a patient support unit;
   b) positioning a mobile tomographic imaging system in a predetermined position relative to the patient support unit with the patient placed on the patient support unit;
   c) imaging at least part of the patient's brain using an imaging unit of the tomographic imaging system, the imaging comprising generating an image describing functioning of a blood vessel system of the patient; and
   d) determining, in dependence on the result of the imaging,
   whether the patient support unit should be rotated relative to the tomographic imaging system with the patient placed on the patient support unit so that the patient is free of the imaging unit in order to conduct a medical intervention on the patient's blood vessel system, or whether the patient support unit may remain in its position relative to the tomographic imaging system with the patient placed on the patient support unit, wherein positioning the tomographic imaging system in a predetermined position relative to the patient support unit comprises fastening the patient support unit with the patient placed on the patient support unit to a pedestal of the tomographic imaging system, the pedestal having a predetermined position relative to the imaging unit of the tomographic imaging system and being rotatable around a vertical axis running through the pedestal and patient support unit and rotatable relative to the imaging unit, wherein the pedestal is an integral part of the mobile tomographic system.

2. The method of claim 1, further comprising:
determining, as a result of the imaging, whether the patient suffers from an ischemic stroke or a hemorrhagic stroke.

3. The method of claim 1, wherein the predetermined position is a fixed position.

4. The method of claim 3, wherein the patient support unit is detachably fastened to the pedestal.

5. The method of claim 1, wherein the imaging unit is a scanner configured to generate a magnetic resonance tomography or a computed x-ray tomography.

6. The method of claim 5, wherein the magnetic resonance tomography is a magnetic resonance-based angiography.

7. The method of claim 5, wherein the computed x-ray tomography is an x-ray-based angiography.

8. The method of claim 7, wherein the x-ray-based angiography is a computed tomography angiography.

9. The method of claim 1, wherein the imaging includes generating an angiography of at least part of the patient's brain.

10. The method of claim 1, wherein the patient support unit is a bed or a flat table.

11. The method of claim 1, wherein the patient support unit is translucent for x-rays.

12. The method of claim 1, wherein positioning the tomographic imaging system in a predetermined position relative to the patient support unit comprises leaving the patient support unit stationary and moving the imaging unit towards the patient support unit.

13. The method of claim 1, wherein if determined that the patient support unit should be rotated relative to the mobile tomographic imaging system with the patient placed on the patient support unit, the medical intervention on the patient's blood vessel system includes at least one of:
systemic lysis therapy, local lysis therapy, angioplasty, stenting, vascular surgery, and inserting a catheter into the patient's blood vessel system, in particular intracerebral catheter placement, for removing a blockage from inside the blood vessel system, by mechanical blood clot retrieval; and
at least one of vascular surgery and inserting a catheter into the patient's blood vessel system, which is intracerebral catheter placement, for stopping a hemorrhage by aneurysm coiling or aneurysm gluing or aneurysm clipping, and direct puncturing of or open surgery on the patient's hemorrhagic area including in particular performing a craniotomy to reduce brain pressure caused by hemorrhage, wherein the direct puncturing or open surgery preferably includes using a catheter which must not come into contact with the blood vessel system.

14. The method of claim 1, wherein the medical intervention is conducted or is not conducted.

15. The method of claim 1, wherein, if it is determined that the patient support unit should be rotated relative to the tomographic imaging system with the patient placed on the patient support unit, the patient support unit is rotated relative to the imaging unit with the patient placed on the patient support unit so that the patient is free of the imaging unit.

16. The method of claim 15, further comprising: rotating, after medical intervention has been conducted and with the patient placed on the patient support unit, the patient support unit around a vertical axis into a position relative to the imaging unit which allows to conduct imaging of at least part of the patient's brain.

17. The method of claim 1, wherein, if it is determined that the patient support unit may remain in its position relative to the tomographic imaging system with the patient placed on the patient support unit, the method further comprises a step of:
conducting a medical intervention on the patient's blood vessel system with the patient support unit remaining in its position relative to the tomographic imaging system with the patient placed on the patient support unit.

18. The method of claim 17, wherein the medical intervention is a systemic lysis therapy.

19. The method of claim 1, wherein the patient support unit is a flat top table, and wherein the pedestal is rotatable around the vertical axis ninety degrees relative to the imaging unit to rotate the flat top table so that the patient is free of the imaging unit in order to conduct the medical intervention.

* * * * *